United States Patent [19]

Punja

[11] Patent Number: 4,868,209

[45] Date of Patent: Sep. 19, 1989

[54] HALOGENATED ESTERS

[75] Inventor: Nazim Punja, Crowthorne, England

[73] Assignee: Imperial Chemical Industries PLC, London, England

[21] Appl. No.: 97,827

[22] Filed: Sep. 17, 1987

Related U.S. Application Data

[60] Continuation of Ser. No. 408,922, Aug. 17, 1982, which is a division of Ser. No. 329,135, Dec. 9, 1981, Pat. No. 4,370,346, which is a continuation-in-part of Ser. No. 211,943, Dec. 1, 1980, Pat. No. 4,405,640.

[30] Foreign Application Priority Data

Dec. 21, 1979 [GB] United Kingdom ............... 7944151
Nov. 20, 1980 [GB] United Kingdom ............... 8037257
Dec. 17, 1980 [GB] United Kingdom ............... 8040400

[51] Int. Cl.$^4$ .............................................. A01N 53/00
[52] U.S. Cl. ....................................... 514/531; 560/124
[58] Field of Search ........................ 560/124; 514/531

[56] References Cited

U.S. PATENT DOCUMENTS

| | | | |
|---|---|---|---|
| 3,792,079 | 2/1974 | D'Orazio | 560/124 |
| 3,973,036 | 8/1976 | Hirano et al. | 560/124 X |
| 4,218,469 | 8/1980 | Fuchs et al. | 560/124 X |
| 4,252,820 | 2/1981 | Lantzsch et al. | 560/124 X |

FOREIGN PATENT DOCUMENTS 45-7073 3/1970 Japan ................................. 564/120

*Primary Examiner*—Robert V. Hines
*Attorney, Agent, or Firm*—Cushman, Darby & Cushman

[57] ABSTRACT

Compounds of formula I wherein $R^1$ and $R^2$ are haloalkyl or halo, X is O, S, S(O), $SO_2$ or $NR_4$ where $R_4$ is H or alkyl, $R^3$ is alkyl and n is 1 to 4, and compositions comprising them, useful as insecticides.

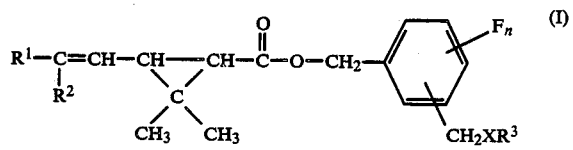

8 Claims, No Drawings

HALOGENATED ESTERS

This is a continuation of application Ser. No. 408,922, filed Aug 17, 1982, a divisional of U.S. application Ser. No. 329,135, filed Dec. 9, 1981, now U.S. Pat. No. 4,370,346, same being a continuation-in-part of Ser. No. 211,943, filed Dec. 1, 1980, now U.S. Pat. No. 4,405,640.

This invention relates to novel cyclopropane derivatives useful as insecticides, to processes for their preparation, to compositions comprising them and to methods of combating insect and similar invertebrate pests using them.

Certain naturally occurring esters of cyclopropane carboxylic acids have long been known to possess insecticidal properties, but these compounds have been too easily degraded by ultra violet light to be of much use in agriculture. Several groups of synthetic compounds based on cyclopropane carboxylic acids (for example those disclosed in British patent specifications Nos. 1,243,858 and 1,413,491) have been evaluated in an attempt to discover compounds of sufficient light stability for use as general agricultural insecticides.

A particularly useful group of such compounds is that disclosed in British patent specification No. 2,000,764 and U.S. Pat. No. 4,183,948. These compounds combine good light stability with excellent contact and residual insecticidal properties, but, in common with the compounds described in British patent specifications 1,243,858 and 1,413,491, they possess little or no fumigant activity. A further group of compounds, halobenzyl esters of 3-(2,2-dihalovinyl)-2,2-dimethylcyclopropane carboxylic acids, is described in U.S. Pat. No. 4,183,950 as having insecticidal properties but there is no indication that the compounds possess fumigant activity.

The present invention relates to certain novel benzyl esters of 3-(2,2-dihalovinyl)-2,2-dimethylcyclopropane carboxylic acids and 3-(2-halo(or trifluoromethyl)-3,3,3-trifluoropropenyl)-2,2-dimethylcyclopropane carboxylic acids with an extremely high level of insecticidal and acaricidal activity which may be used not only as contact or residual insecticides but also as fumigant insecticides.

Accordingly this invention provides compounds of formula:

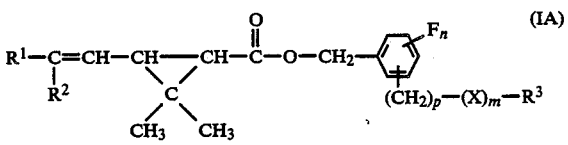

wherein $R^1$ and $R^2$ are each selected from methyl, halomethyl, and halo; X is oxygen, sulphur, sulphinyl, sulphonyl or a group $NR^4$ where $R^4$ represents hydrogen, lower alkyl or lower carboxylic acyl; $R^3$ is lower alkyl, lower alkenyl, phenyl or benzyl, and additionally $R^3$ may be hydrogen when X is a group $NR^4$; and n has a value from one to four, and each of m and p has the value zero or one.

The term "lower" is used herein in relation to "alkyl", "alkenyl" and "carboxylic acyl" groups to indicate such groups containing up to six carbon atoms, although such groups containing up to four carbon atoms are generally preferred.

In a preferred aspect the invention provides compounds of formula:

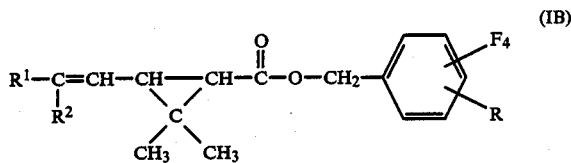

wherein $R^1$ and $R^2$ are both methyl, chloro or bromo, or one of $R^1$ and $R^2$ is fluoro or chloro and the other is trifluoromethyl, and R is alkoxymethyl of up to 4 carbon atoms in the alkoxy moiety, alkylthiomethyl of up to 4 carbon atoms in the alkylthio moiety, phenoxy, or dialkylaminomethyl of up to 4 carbon atoms in each alkyl moiety. Amongst this group of compounds there are especially preferred those wherein $R^1$ and $R^2$ are both chloro, or one of $R^1$ and $R^2$ is chloro and the other is trifluoromethyl, and R is methoxymethyl, ethoxymethyl, n-propoxymethyl, phenoxymethyl, diethylaminomethyl or ethylthiomethyl. R is preferably in the 4- position with respect to the cyclopropane ester group.

Particular compounds according to the invention as defined by formula IA above include those set out in Table I herein in which the meanings for $R^1$, $R^2$ and R are given for each compound.

TABLE I

| Compound No. | $R^1$ | $R^2$ | R |
|---|---|---|---|
| 1 | $CF_3$ | Cl | 4-$CH_2OCH_3$ |
| 2 | $CF_3$ | Cl | 4-$CH_2OC_2H_5$ |
| 3 | $CF_3$ | Cl | 4-$CH_2OC_3H_7(n)$ |
| 4 | Cl | Cl | 4-$CH_2OCH_3$ |
| 5 | $CF_3$ | Cl | 4-$CH_2OC_6H_5$ |
| 6 | $CF_3$ | Cl | 4-$CH_2SC_2H_5$ |
| 7 | $CF_3$ | Cl | 4-$CH_2N(C_2H_5)_2$ |
| 8 | Cl | Cl | 4-$CH_2OC_2H_5$ |
| 9 | Cl | Cl | 4-$CH_2OCH_2CH=CH_2$ |
| 10 | $CF_3$ | Cl | 4-$CH_2OCH_2CH=CH_2$ |
| 11 | $CF_3$ | Cl | 4-$CH_2N(CH_3)_2$ |
| 12 | $CF_3$ | Cl | 4-$CH_2SO_2C_2H_5$ |
| 13 | $CF_3$ | Cl | 4-$CH_2NHCH_3$ |
| 14 | $CF_3$ | Cl | 4-$CH_2NHC_2H_5$ |
| 15 | $CF_3$ | Cl | 4-$CH_2SCH_3$ |
| 16 | $CF_3$ | Cl | 4-$CH_2S(O)CH_3$ |
| 17 | $CF_3$ | F | 4-$CH_2OCH_3$ |

It will be appreciated by those skilled in the art that the compounds represented by formula I are capable of existing in various geometrical and stereoisomeric forms. Thus there may be cis and trans isomers arising from the substitution pattern of the cyclopropane ring, and E- and Z-isomers arising from the substituted vinyl group when $R^1$ is not identical with $R^2$. In addition two of the three carbon atoms of the cyclopropane are capable of existing in either R- or S-configurations since they are asymmetrically substituted. Within the group of compounds represented by Formula I the cis isomers usually have better insecticidal properties than the trans isomers or the mixture of cis and trans isomers; the (+)-cis isomers being particularly preferred.

A particularly useful single isomer of a compound according to the invention is the 4-methoxymethyltetrafluorobenzyl ester of (+)-cis-3-(Z-2-chloro-3,3,3-trichloroprop-1-en-yl)-2,2-dimethylcyclopropane carboxylic acid, which is believed to have the (1R,3R) configuration in the cyclopropane ring.

The compounds of the invention according to Formula I are esters and may be prepared by conventional esterification processes, of which the following are examples.

(a) An acid of formula:

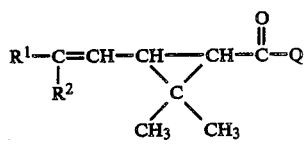

where Q represents the hydroxy group and $R^1$ and $R^2$ have any of the meanings given hereinabove, may be reacted directly with an alcohol of formula:

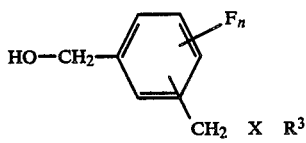

where X, $R^3$ and m have any of the meanings given hereinabove, the reaction preferably taking place in the presence of an acid catalyst, for example, dry hydrogen chloride.

(b) An acid halide of formula II where Q represents a halogen atom, preferably a chlorine atom, and $R^1$ and $R^2$ have any of the meanings given hereinabove, may be reacted with an alcohol of formula III, the reaction preferably taking place in the presence or a base, for example, pyridine, alkali metal hydroxide or carbonate, or alkali metal alkoxide.

(c) An acid of formula II where Q represents the hydroxy group or, preferably, an alkali metal salt thereof, may be reacted with halide of formula:

where $Q^1$ represents a halogen atom, preferably the bromine or chlorine atom, X, $R^3$ and n have any of the meanings given hereinabove, or with the quaternary ammonium salts derived from such halides with tertiary amines, for example pyridine, or trialkyl amines such as triethylamine.

(d) A lower alkyl ester of formula (II) where Q represents a lower alkoxy group containing up to six carbon atoms, preferably the methoxy or ethoxy group, and $R^1$ and $R^2$ have any of the meanings given hereinabove, is heated with an alcohol of formula III to effect a transesterification reaction. Preferably the process is performed in the presence of a suitable catalyst, for example, an alkali metal alkoxide, such as sodium methoxide, or an alkylated titanium derivative, such as tetramethyl titanate.

All of these conventional processes for the preparation of esters may be carried out using solvents and diluents for the various reactants where appropriate, and may be accelerated or lead to higher yields of product when performed at elevated temperatures or in the presence of appropriate catalysts, for example phase-transfer catalysts.

The preparation of individual isomers may be carried out in the same manner but commencing from the corresponding individual isomers of compounds of formula II. These may be obtained by conventional isomer separation techniques from mixtures of isomers. Thus cis and trans isomers may be separated by fractional crystallisation of the carboxylic acids or salts thereof, whilst the various optically active species may be obtained by fractional crystallisation of salts of the acids with optically active amines, followed by regeneration of the optically pure acid. The optically pure isomeric form of the acid (or its equivalent acid chloride or ester) may then be reacted with the appropriate alcohol to produce a compound of formula I in the form of an individually pure isomer thereof.

The preparation of the compounds of formula II wherein Q is hydroxy, alkoxy or halo, and $R^1$ and $R^2$ are as defined hereinabove, useful as intermediates in the preparation of the compounds of the invention, is fully described in British Patent Specification No. 2,000,764 and in U.S. Pat. No. 4,183,948, or British Patent Specification No. 1,413,491.

The compounds of formulae III are believed not to have been described before. In a further aspect therefore the invention provides compounds of formula III wherein X, $R^3$ and n have any of the meanings given for the corresponding compounds of formula I, including, in particular those set out in Table II below which corresponds to the formula:

TABLE II $$\text{HO-CH}_2\text{-C}_6\text{F}_4\text{-CH}_2\text{-X-R}^3$$

| Compound | X | $R^3$ | Compound | X | $R^3$ |
|---|---|---|---|---|---|
| A | O | $CH_3$ | H | NH | $CH_3$ |
| B | O | $C_2H_5$ | J | NH | $C_2H_5$ |
| C | O | $C_3H_7(n)$ | K | $NCH_3$ | $CH_3$ |
| D | O | $C_6H_5$ | L | $SO_2$ | $C_2H_5$ |
| E | S | $C_2H_5$ | M | S | $CH_3$ |
| F | $NHC_2H_5$ | $C_2H_5$ | N | S(O) | $CH_3$ |
| G | O | $CH_2CH=CH_2$ | | | |

The compounds of formula III may be prepared by a sequence of reactions, each stage of which is conventional in itself, such as those set forth by way of example in the following scheme. Further details of the various reactions involved are fully illustrated in the Examples herein.

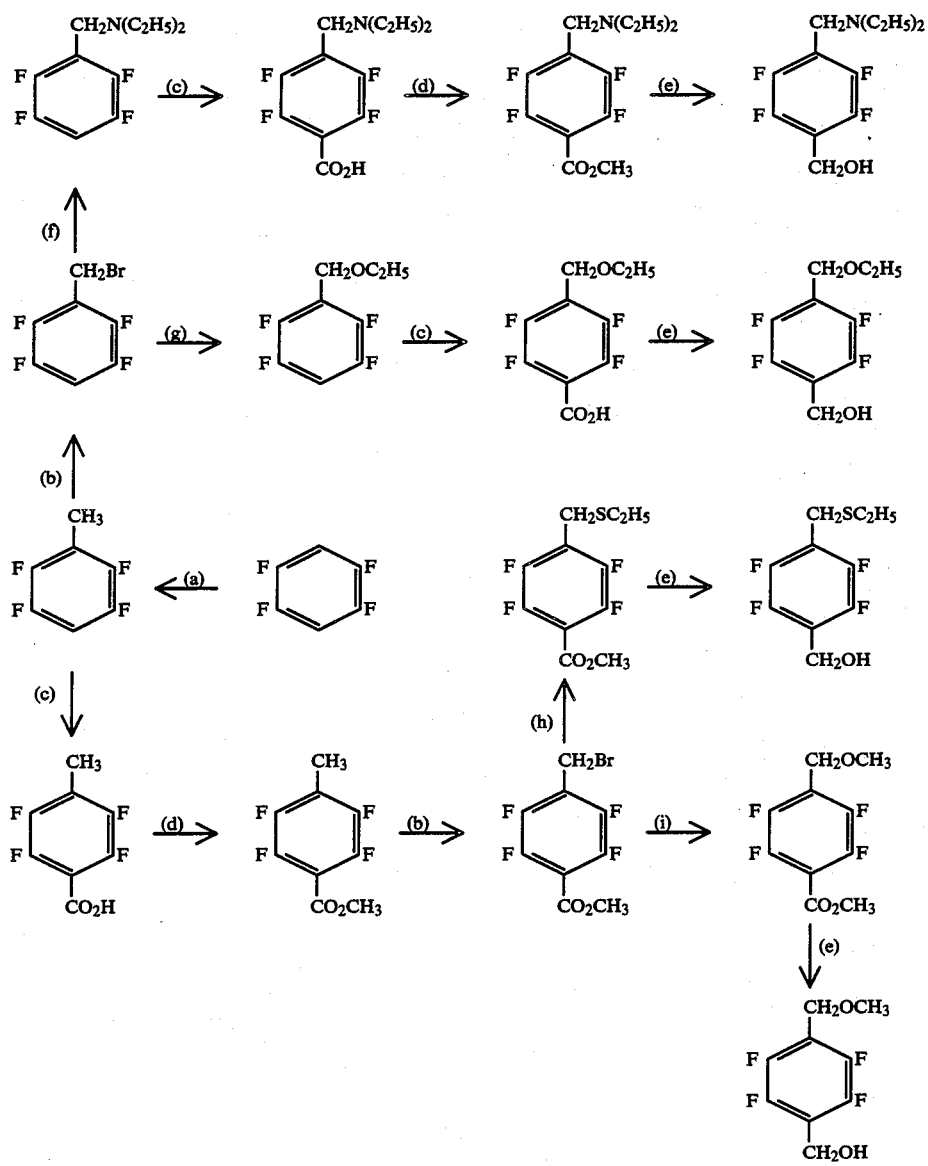

Key to Reagents
(a) Lithium butyl/methyl iodide
(b) N—Bromo succinimide
(c) Lithium butyl/carbon dioxide
(d) Thionyl chloride/methanol
(e) Lithium aluminium hydride
(f) Diethylamine
(g) Sodium ethoxide/ethanol
(h) Sodium ethylmercaptide
(i) Sodium methoxide When the processes for preparing the compounds of Formula I are performed using intermediates which are themselves mixtures of isomers the products obtained will also be mixtures of isomers. Thus, the product would be a mixture of (±)-cis and (±)-trans isomers (perhaps with one form predominating) if the intermediate acid or acid derivative was used in the form of a mixture of (±)-cis and (±)-trans isomers. If a single isomer, of the acid, e.g. the (+)-cis isomer with Z-configuration in the 2-chloro-3,3,3-trifluoropropenyl group, was used, the product would also be the single isomer of that stereochemical configuration, or a pair of isomers if there is an asymmetric carbon atom in the alcohol moiety.

In order to avoid confusion the products obtained by the processes described in the Examples herein are referred to as Products I to XV, each product being defined in terms of isomeric composition with reference to the compounds of Table I as follows:

Product I: 4-methoxymethyltetrafluorobenzyl 3-(2-chloro-3,3,3-trifluoroprop-1-en-1-yl)-2,2-dimethylcyclopropane carboxylate (compound No. 1, Table I) consisting of 100% w/w of the (±)-Z-cis isomer.

Product II: 4-ethoxymethyltetrafluorobenzyl 3-(2-chloro-3,3,3-trifluoroprop-1-en-1-yl)-2,2-dimethylcyclopropane carboxylate (compound No. 2, Table I) consisting of 100 w/w of the (±) -Z-cis isomer.

Product III: 4-n-propoxymethyltetrafluorobenzyl 3-(2-chloro-3,3,3-trifluoroprop-1-en-1-yl)-2,2-dimethylcyclopropane carboxylate (compound No. 3, Table I) consisting of 100% w/w of the (±)-Z-cis isomer.

Product IV: 4-methoxymethyltetrafluorobenzyl 3-(2,2-dichlorovinyl)-2,2-dimethylcyclopropane carboxylate (compound No.4, Table I) consisting of 50% w/w of the (±)-cis isomer and 50% w/w of the (±)-trans isomer Product V: 4-phenoxymethyltetrafluorobenzyl 3-(2-chloro-3,3,3-trifluoroprop-1-en-1-yl)-2,2-dimethylcyclopropane carboxylate (compound No. 5, Table I) consisting of 100% w/w of the (±)-Z-cis isomer.

Product VI: 4-ethylthiomethyltetrafluorobenzyl 3-(2-chloro-3,3,3-trifluoroprop-1-en-1-yl)-2,2-dimethylcyclopropane carboxylate (compound No. 6, Table I) consisting of 100% w/w of the (±)-Z-cis isomer.

Product VII: 4-diethylaminomethyltetrafluorobenzyl 3-(2-chloro-3,3,3-trifluoroprop-1-en-1-yl)-2,2-dimethylcyclopropane carboxylate (compound No. 7, Table I) consisting of 100% w/w of the (±)-Z-cis isomer.

Product VIII: 4-dimethylaminomethyltetrafluorobenzyl 3-(2-chloro-3,3,3-trifluoroprop-1-en-1-yl)-2,2-dimethylcyclopropane carboxylate (compound No. 11, Table I) consisting of 100% w/w of the (±)-Z-cis isomer.

Product IX: 4-ethanesulphonylmethyltetrafluorobenzyl 3-(2-chloro-3,3,3-trifluoroprop-1-en-1-yl)-2,2-dimethylcyclopropane carboxylate (compound No. 12, Table I) consisting of 100% w/w of the (±)-Z-cis isomer.

Product X: 4-methylaminomethyltetrafluorobenzyl 3-(2-chloro-3,3,3-trifluoroprop-1-en-1-yl)-2,2-dimethylcyclopropane carboxylate (compound No. 13, Table I) consisting of 100% w/w of the (±)-Z-cis isomer.

Product XI: 4-ethylaminomethyltetrafluorobenzyl 3-(2-chloro-3,3,3-trifluoroprop-1-en-1-yl)-2,2-dimethylcyclopropane carboxylate (compound No. 14, Table I) consisting of 100% w/w of the (±)-Z-cis isomer.

Product XII: 4-methylthiomethyltetrafluorobenzyl 3-(2-chloro-3,3,3-trifluoroprop-1-en-1-yl)-2,2-dimethylcyclopropane carboxylate (compound No. 15, of Table I) consisting of 100% w/w of the (±)-Z-cis isomer.

Product XIII: 4-methanesulphinylmethyltetrafluorobenzyl 3-(2-chloro-3,3,3-trifluoroprop-1-en-1-nyl)-2,2-dimethylcyclopropane carboxylate (compound No. 16, of Table I) consisting of 100% w/w of the (±)-Z-cis isomer.

Product XIV: 4-methoxymethyltetrafluorobenzyl 3-(2,3,3,3-tetrafluoroprop-1-en-1-yl)-2,2-dimethylcyclopropane carboxylate (compound No. 17, Table I) consisting of 100% w/w of the (±)-Z-cis isomer.

Product XV: 4-methoxymethyltetrafluorobenzyl 3-(2,3,3,3-tetrafluoroprop-1-en-1-yl)-2,2-dimethylcyclopropane carboxylate (compound No 17, Table I) consisting of a mixture of ca. 10% w/w of the (±)-Z-cis isomer and ca. 90% w/w of the (±)-Z-trans isomer.

The compounds of formula I may be used to combat and control infestations of insect pests and also other invertebrate pests, for example, acarine pests. The insect and acarine pests which may be combatted and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise a insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice, gypsum or corn cob granules. Granules are particularly useful for combating soil borne insect pests, such as root worms of the genus Diabrotica, cutworms (Agrotis spp.) and wireworms (Agriotis spp.). Preferably, the granules contain from 1 to 2.5% by weight of the active ingredient, which is absorbed onto the granule by, for example, spraying the granules with a solution of the active ingredient in a volatile solvent which is subsequently evaporated from the surface of the granules. Such solutions may contain other ingredients, for example a resin to regulate the rate of release of the active ingredient from the granules, or to help prevent premature disintegration of the granules. Granules may be applied to the soil either in a band between the furrows defining the crop rows, or broadcast, and may if desired be lightly incorporated in the soil, or they may be placed in the furrows themselves at the time of planting the crop. Application of granules at a rate of from 5 to 25 lb/acre (approximately 5 to 25 kg/ha) is usually sufficient to control the pests, and a preferred rate is within the range 8 to 15 lb/acre (approximately 8 to 15 kg/ha) based on the active ingredient.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the nonionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:
*Aphis fabae* (aphids)
*Megoura viceae* (aphids)
*Aedes aegypti* (mosquitoes)
*Dysdercus fasciatus* (capsids)
*Musca domestica* (houseflies)
*Pieris brassicae* (white butterfly, larvae)
*Plutella maculipennis* (diamond back month, larvae)
*Phaedon cochleariae* (mustard beetle)
*Telarius cinnabarinus* (carmine spider mite)
*Aonidiella* spp. (scale insects)
*Trialeuroides* spp. (white flies)
*Blattella germanica* (cockroaches)
*Spodoptera littoralis* (cotton leaf worm)
*Chortiocetes terminifera* (locusts)
*Diabrotica* spp. (rootworms)
*Agrotis* spp. (cutworms)

The compounds of formula I and compositions comprising them have shown themselves to be particularly useful in controlling lepidopteran pests of cotton, for example Spodoptera spp. and Heliothis spp. The fumigant properties of the compounds enable them to be used to combat pests which inhabit the soil, for example Diabrotica spp. They are also excellent knock down agents and as such may be used in conjunction with other insecticides to combat public health pests such as flies. They are also very useful in combatting insect and acarine pests which infest domestic animals, such as *Lucilia sericata*, and ixodid ticks such as Boophilus spp., Ixodes spp., Amblyomma spp., Rhipicephalus spp., and Dermaceutor spp. They are effective in combatting both susceptible and resistant strains of these pests in their adult, larval and intermediate stages of growth, and may be applied to the infested host animal by topical, oral or parenteral administration.

The following Examples illustrate the various aspects of the invention.

EXAMPLE 1

This Example illustrates the insecticidal properties of the Products I to VII.

The activity of the products was determined using a variety of insect pests. The product was used in the form of liquid preparations containing 500, 100, 50 or 25 parts per million (p.p.m.) by weight of the product. The preparations were made by dissolving the product in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the product. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment. Details are given in Table III.

The results of the tests are given in Table IV for each of the products I to VII at the rate in parts per million given in the second column as a grading of mortality on a scale of 0–9 wherein

| 0 | represents | less than 10% | mortality |
|---|---|---|---|
| 1 | " | from 10 to 19% | " |
| 2 | " | from 20 to 29% | " |
| 3 | " | from 30 to 39% | " |
| 4 | " | from 40 to 49% | " |
| 5 | " | from 50 to 59% | " |
| 6 | " | from 60 to 69% | " |
| 7 | " | from 70 to 79% | " |
| 8 | " | from 80 to 89% | " |
| 9 | " | from 90 to 100% | " |

In Table IV the pest organism used is designated by a letter code and the pest species, the support medium or food, and the type and duration of test is given in Table III.

TABLE III

| CODE LETTERS (Table IV) | PEST SPECIES | SUPPORT MEDIUM/FOOD | TYPE OF TEST* | DURATION (days) |
|---|---|---|---|---|
| MD | *Musca domestica* (houseflies - adults) | Cotton wool/ milk, sugar | Contact | 2 |
| SL | *Spodoptera littoralis* | Cotton leaves | Residual | 1 |

TABLE III-continued

| CODE LETTERS (Table IV) | PEST SPECIES | SUPPORT MEDIUM/FOOD | TYPE OF TEST* | DURATION (days) |
|---|---|---|---|---|
| PX | (cotton leaf worm - larvae) *Plutella xylostella* (diamond back moth - larvae) | Mustard leaves | Residual | 3 |
| SG | *Sitophilus granarius* (grain weevil - adults) | Grain | Contact | 3 |
| DB | *Diabrotica balteata* (rootworm - larvae) | Filter paper | Contact | 3 |

*"Contact" test indicates that both pests and medium were treated and "residual" indicates that the medium was treated before infestation with the pests.

TABLE IV

| PRODUCT | RATE (ppm) | PEST SPECIES ||||| 
|---|---|---|---|---|---|---|
| | | MD | SL | PX | SG | DB |
| I | 50 | 9 | 9 | 9 | 9 | 9 |
| II | 100 | 9 | 9 | 9 | 9 | 9 |
| III | 500 | 9 | 9 | 9 | 9 | 9 |
| IV | 100 | 9 | 9 | 9 | 9 | 9 |
| V | 100 | — | 9 | 9 | 0 | 3 |
| VI | 50 | 9 | 9 | 9 | 9 | 9 |
| VII | 100 | 9 | 9 | 9 | 9 | 9 |
| VIII | 100 | — | 9 | 9 | 9 | 9 |
| IX | 100 | 5 | 9 | 0 | 0 | 2 |
| X | 100 | 9 | 9 | 9 | 0 | 2 |
| XI | 100 | 9 | 9 | 9 | 0 | 9 |
| XII | 100 | 9 | 9 | 9 | 9 | 9 |
| XIII | 100 | 9 | 0 | 6 | 0 | 5 |
| XIV | 100 | 9 | 9 | 9 | — | 9 |
| XV | 100 | 9 | 9 | 9 | — | 9 |

A dash (—) in Table IV above indicates that the Product had not been tested against the particular pest species.

In further tests the products showed insecticidal activity against a number of other species. Thus for example Product VII, showed good aphicidal properties against *Aphis fabae*.

In Table V below the minimum concentration (in parts per million) required to give 100% mortality of red spider mite adults (*Tetranychus telarius*, SM) on French bean leaves and plant hoppers (*Nilaparvata lugens*, PH) on rice is given for several of the Products. A dash (—) in this table indicates that 100% mortality was not obtained at the highest rate tested (usually 500 parts per million).

TABLE V

| Product | Rate (ppm) giving 100% mortality ||
|---|---|---|
| | SM | PH |
| I | 100 | 100 |
| II | 100 | 100 |
| III | — | 500 |
| VII | — | 100 |

EXAMPLE 2

This Example illustrates the preparation of 2,3,5,6-tetrafluorotoluene.

A solution of n-butyllithium in hexane (1.6M, 62.5 ml) was added dropwise to a well stirred solution of 1,2,4,5-tetrafluorobenzene (15.0 g) in dry tetrahydrofuran (150 ml) maintained at a temperature of −60° C. under an atmosphere of dry argon. When the addition was complete the mixture was stirred at −45° C. for 2 hours and then methyl iodide (14.2 g) was added dropwise whilst the temperature was kept at −45° C. After a period of 30 minutes the mixture was allowed to warm to the ambient temperature, poured into distilled water and the mixture extracted with diethyl ether (2×50 ml), and the extracts dried over anhydrous magnesium sulphate. After filtering the solution was concentrated by evaporation of the solvents at atmospheric pressure. The residual oil was distilled and the fraction boiling in the range 117°–121° C. at atmospheric pressure 6.0 g) collected, identified by n.m.r. and gas chromatographic analysis as consisting of ca. 95% of the required 2,3,5,6-tetrafluorotoluene and ca. 5% of 2,3,5,6-tetrafluoro-1,4-xylene.

N.m.r. ($^1$H(ppm)CDCl$_3$): 2.28(t,3H); 6.58–6.94 (m,1H). Infra red (liquid film): 3075, 1645, 1510, 1255, 1165 cm$^{-1}$.

EXAMPLE 3

This example illustrates the preparation of 2,3,5,6-tetrafluoro-4-toluic acid.

The product of Example 2 above (5.5 g) was mixed with diethyl ether (35 ml), the mixture cooled to −70° C., and maintained at this temperature whilst a solution of n-butyllithium in h-hexane (1.6M, 21 ml) was slowly added. The mixture was stirred for a period of 1 hour during which time a fine white precipitate was formed. Dry carbon dioxide gas was then passed into the mixture for 30 minutes whilst the temperature was maintained within the range −70° C. to −40° C., and continued to be passed in thereafter whilst the mixture was allowed to warm to the ambient temperature.

After acidifying with dilute hydrochloric acid (6N, 40 ml) the organic phase was separated, washed with water and dried over anhydrous magnesium sulphate. After evaporation of the solvents under reduced pressure the residual oil (which from n.m.r. analysis was shown to be an approximately 1:1 mixture of the desired product and pentanoic acid) was carefully distilled under reduced pressure (water pump) using a Kugelrohr apparatus, and the fraction which solidified on cooling collected and recrystallised from toluene to yield 2,3,5,6-tetrafluoro-4-toluic acid, m.p. 170° C. (0.65 g), identified by infra red and nuclear magnetic resonance spectroscopy.

N.m.r. ($^1$H(ppm)CDCl$_3$): 2.44(t,3H); 11.56 (s,1H). Infra red (liquid paraffin): 3300–2450,, 1710, 1650, 1460, 1070 cm$^{-1}$.

EXAMPLE 4

This example illustrates the preparation of 2,3,5,6-tetrafluorobenzyl bromide.

A mixture of 2,3,5,6-tetrafluorotoluene (1.7 g), N-bromosuccinimide (1.9 g), dry carbon tetrachloride (10 ml) and benzoyl peroxide (0.01 g) was heated at the reflux temperature for 20 hours, cooled to the ambient temperature (ca. 25° C.) filtered and the filtrate diluted with diethyl ether. The ethereal solution was washed with water, dried over anhydrous magnesium sulphate and concentrated by evaporation of the solvents to yield 2,3,5,6-tetrafluorobenzyl bromide as a mobile colourless oil.

EXAMPLE 5

This Example illustrates the preparation of methyl 4-methyl 2,3,5,6-tetrafluorobenzoate.

A mixture of 2,3,5,6-tetrafluoro-4-toluic acid (1.0 g), methyl alcohol (5 ml) and concentrated sulphuric acid (0.25 ml) was heated at the reflux temperature for 10 hours, cooled to the ambient temperature (ca. 25° C.) and poured into iced water. The resultant mixture was extracted with diethyl ether, the extracts washed with water, dried over anhydrous magnesium sulphate and concentrated by evaporation of the ether under reduced pressure. The residual oil was shown by infra red analysis (liquid film: 1740 cm$^{-1}$) and N.m.r. spectroscopy to be the required methyl 4-methyl 2,3,5,6-tetrafluorobenzoate.

EXAMPLE 6

This Example illustrates the preparation of N,N-diethyl-2,3,5,6-tetrafluorobenzylamine.

A solution of diethylamine (0.6 g) in dry diethyl ether (2.0 ml) was added slowly to a stirred solution of 2,3,5,6-tetrafluorobenzyl bromide (2.0 g) in diethyl ether (30 ml) at the ambient temperature (ca. 25° C.), and the resultant mixture stirred for a further 6 hours and then kept at the ambient temperature for a further 18 hours. After removal of the ether by evaporation water containing a few drops of dilute hydrochloric acid was added to the residue and the mixture obtained washed with ether, made basic with saturated sodium bicarbonate solution and extracted with ether. The ethereal extracts were washed with water, dried over anhydrous magnesium sulphate and concentrated by evaporation of the ether. The residual oil was shown by infra red and N.m.r. spectroscopy to be N,N-diethyl-2,3,5,6-tetrafluorobenzylamine.

EXAMPLE 7

The procedure of Example 3 was used to convert diethylaminomethyl-2,3,5,6-tetrafluorobenzene to 4-diethylaminomethyl-2,3,5,6-tetrafluorobenzoic acid.

EXAMPLE 8

The procedure of Example 5 was used to convert diethylaminomethyl-2,3,5,6-tetrafluorobenzoic acid to its methyl ester.

EXAMPLE 9

This Example illustrates the preparation of 4-diethylaminomethyl-2,3,5,6-tetrafluorobenzyl alcohol.

Lithium aluminium hydride (50 mg) was added carefully to a stirred solution of methyl 4-diethylamino-2,3,5,6-tetrafluorobenzoate (0.79 g) in dry diethyl ether (10 ml) at the ambient temperature. After 1 hour the mixture was heated at the reflux temperature for 7 hours after which the mixture was cooled and partitioned between more ether and water. The ethereal phase was separated and combined with a further ethereal extract of the aqueous phase. The combined extracts were washed with water, dried over anhydrous magnesium sulphate, and the ether removed by evaporation under reduced pressure. The residual oil was purified by preparative thick layer chromatography using 2 mm thick silica gel and a 1:1 ether/petroleum ether mixture as eluent. The required product as obtained (after removal from the plate of the component of largest Rf value) by extraction of the silica with chloroform methyl alcohol mixture and identified by N.m.r. and infra red spectroscopy.

N.m.r. (CDCl$_3$): 1.10 (t,6H); 2.54 (q,4H); 3.75 (m,2H); 4.04 (S,1H); 4.72 (m,2H) ppm.

Infra red (liquid fim): 3600–3100, 2980, 1490, 1280, 1050, 880 cm$^{-1}$.

EXAMPLE 10

This Example illustrates the preparation of ethyl 2,3,5,6-tetrafluorobenzyl ether.

2,3,5,6-tetrafluorobenzyl bromide (2.43 g) was added to a stirred solution of sodium (0.27 g) in ethyl alcohol (20 ml) at the ambient temperature, and the mixture stirred for a further 90 minutes. After keeping at the ambient temperature for 18 hours the mixture was poured into an excess of water and the resultant mixture extracted three times with diethyl ether. The combined extracts were washed with water, dried over anhydrous magnesium sulphate and concentrated by evaporation of the volatile portion under reduced pressure. The residual oil (1.6 g) was shown N.m.r. and infra red spectroscopy to be the required product.

EXAMPLE 11

The procedure of Example 10 was used to prepare other compounds from α-bromo-2,3,5,6-tetrafluorotoluene, and the appropriate hydroxy compound as follows:
(i) n-propoxymethyl-2,3,5,6-tetrafluorobenzene
(ii) phenoxymethyl-2,3,5,6-tetrafluorobenzene.

EXAMPLE 12

The procedure of Example 3 was used to prepare the following benzoic acids from the appropriate precursors as follows:
(i) 4-ethoxymethyl-2,3,5,6-tetrafluorobenzoic acid
(ii) 4-n-propoxymethyl-2,3,5,6-tetrafluorobenzoic acid
(iii) 4-phenoxymethyl-2,3,5,6-tetrafluorobenzoic acid.

EXAMPLE 13

The procedure of Example 9 was used to reduce the appropriate benzoic acids to the following benzyl alcohols:
(i) 4-ethoxymethyl-2,3,5,6-tetrafluorobenzyl alcohol.

N.m.r. (CDCl$_3$): 1.20 (t,3H); 2.82 (s,1H); 3.58 (q,2H); 4.61 (m,2H); 4.76 (m,2H) ppm.

Infra red (liquid film): 3600–3100, 2980, 1490, 1290, 1060, 880 cm$^{-1}$.

(ii) 4-n-propoxymethyl-2,3,5,6-tetrafluorobenzyl alcohol.

N.m.r. (CDCl$_3$): 0.92 (t,3H); 1.60 (q,2H); 3.46 (m,3H); 4.60 (m,2H); 4.77 (m,2H) ppm.

Infra red (liquid film): 3600–3100, 2980, 1490, 1290, 1060, 880 cm$^{-1}$.

(iii) 4-phenoxymethyl-2,3,5,6-tetrafluorobenzyl alcohol.

N.m.r. (CDCl$_3$): 2.10 (s,1H); 4.60 (m,2H); 5.10 (m,2H); 6.85–7.38 (m,5H) ppm.

Infra red (liquid film): 3600–3100, 2590, 1600, 1490, 1290, 1060, 1040, 890 cm$^{-1}$.

EXAMPLE 14

The procedure of Example 4 was used to convert the methyl ester of 2,3,5,6-tetrafluoro-4-toluic acid into methyl 4-bromomethyl-2,3,5,6-tetrafluorobenzoate.

EXAMPLE 15

The procedure of Example 10 was used to prepare the following compounds from methyl 4-bromomethyl-2,3,5,6-tetrafluorobenzoate and the appropriate alcohol or thiol.

(i) methyl 4-methoxymethyl-2,3,5,6-tetrafluorobenzoate.

(ii) methyl 4-ethylthiomethyl-2,3,5,6 tetrafluorobenzoate.

EXAMPLE 16

The procedure of Example 9 was used to obtain the following benzyl alcohols by reduction of the appropriate methyl esters as follows:

(i) 4-methoxymethyl-2,3,5,6-tetrafluorobenzyl alcohol.

N.m.r. (CDCl$_3$): 2.82 (s,1H); 3.44 (s,3H); 4.64 (s,2H); 4.86 (s,2H) ppm.

Infra red (liquid film): 3650-3000, 1650, 1490, 1280, 1080, 1050 cm$^{-1}$.

(ii) 4-ethylthiomethyl-2,3,5,6-tetrafluorobenzyl alcohol.

N.m.r. (CDCl$_3$): 1.26 (t,3H); 2.00 (s,1H); 2.54 (q,2H); 3.78 (s,2H); 4.78 (s,2H) ppm.

Infra red (liquid film): 3650-3000, 1655, 1490, 1010, 945 cm$^{-1}$.

EXAMPLE 17

This Example illustrates the preparation of 4-methoxymethyl-2,3,5,6-tetrafluorobenzyl (±)-3-(Z-2-chloro-3,3,3-trifluoro-prop-1-en-1-yl)-2,2-dimethylcyclopropane carboxylate (Product I).

A mixture of thionyl chloride (3.0 ml) and (±)-3-(Z-2-chloro-3,3,3-trifluoroprop-1-en-1-yl)-2,2-dimethylcyclopropane carboxylic acid, (0.200 g) was heated at the reflux temperature for 5 hours, and then kept at the ambient temperature for 16 hours. After removing the excess thionyl chloride by evaporation under reduced pressure (the last traces being removed by azeotropic distillation with toluene) the resultant acid chloride was added to a mixture of 4-methoxymethyltetrafluoro-benzyl alcohol (0.18 g), dry pyridine (0.065 g) and dry toluene (10 ml), and the resultant mixture stirred at the ambient temperatures for 2 hours and then stood at the ambient temperature for a further 16 hours. After adding toluene (10 ml) the mixture was washed successively with dilute hydrochloric acid (2N, 20 ml), water and saturated sodium bicarbonate solution, dried over anhydrous magnesium sulphate and concentrated by evaporation of the solvent under reduced pressure. The residual oil was purified by preparative thick layer chromatography (2 mm thick silica gel/chloroform eluent) to give 4-methoxymethyl-2,3,5,6-tetrafluorobenzyl (±)-3-(Z-2-chloro-3,3,3-trifluoroprop-1-en-1-yl)-2,2-dimethylcyclopropane carboxylate, identified by n.m.r. and infra red spectroscopy.

N.m.r. ($^1$H(ppm)CDCl$_3$): 1.28 (s,6H); 1.90-2.36 (m,2H); 3.44 (s,3H); 4.64 (s,2H); 5.30 (s,2H); 6.96 (d,1H).

Infra red (liquid film): 3080, 1735, 1650, 1490, 1135 cm$^{-1}$.

EXAMPLE 18

The procedure of Example 17 was used to prepare the following products from either (±)-cis-3-(Z-2-chloro-3,3,3-trifluoroprop-1-en-1yl)-2,2-dimethylcyclopropane carboxylic acid or (±) -cis/trans-3-(2,2-dichlorovinyl)-2,2-dimethylcyclopropane carboxylic acid and the appropriate benzyl alcohol.

(i) 4-ethoxymethyl-2,3,5,6-tetrafluorobenzyl (±)-cis-3-(Z-2-chloro-3,3,3-trifluoroprop-len-1yl)-2,2-dimethylcyclopropane carboxylate.

N.m.r. (CDCl$_3$): 1.22 (t,3H); 1.30 (s,6H); 1.90-2.27 (m,2H); 3.58 (q,2H); 4.62 (m,6H); 5.22 (m,2H); 6.88 (d,1H) ppm.

Infra red (liquid film): 2980, 1730, 1650, 1490, 1290, 1200, 1135 cm$^{-1}$.

(ii) 4-n-propoxymethyl-2,3,5,6-tetrafluorobenzyl (±)-cis-3-(Z-2-chloro-3,3,3-trifluoroprop-1-en-1yl)-2,2-dimethylcyclopropane carboxylate.

N.m.r. (CDCl$_3$): 0.92 (t,3H); 1.30 (s,6H); 1.60 (q,2H); 1.90-2.27 (m,2H); 3.46 (t,2H); 4.60 (m,2H); 5.22 (m,2H); 6.88 (d,1H) ppm.

Infra red (liquid film): 2980, 1730, 1650, 1490, 1290, 1200, 1140, 960 cm$^{-1}$.

(iii) 4-methoxymethyl-2,3,5,6-tetrafluorobenzyl (±)-cis/trans-3-(2,2-dichlorovinyl)-2,2-dimethylcyclopropane carboxylate.

N.m.r. (CDCl$_3$): 1.18-1.38 (m,6H); 1.58-2.36 (m,2H); 3.44 (s,3H); 4.60 (s,2H); 5.24 (s,2H); 5.66, 6.14 (2d,1H) ppm.

Infra red (liquid film): 3080, 1735, 1655, 1495, 1135 cm$^{-1}$.

(iv) 4-phenoxymethyl-2,3,5,6-tetrafluorobenzyl (±)-cis-3-(Z-2-chloro-3,3,3-trifluoroprop-1-en-1yl)-2,2-dimethylcyclopropane carboxylate.

N.m.r. (CDCl$_3$): 1.30 (s,6H); 1.90-2.27 (m,2H); 5.10 (m,2H); 5.18 (m,2H); 6.80-7.40 (m,6H) ppm.

Infra red (liquid film): 2980, 1730, 1650, 1600, 1490, 1290, 1200, 1140 cm$^{-1}$.

(v) 4-diethylaminomethyl-2,3,5,6-tetrafluorobenzyl (±)-cis-3-(Z-2-chloro-3,3,3-trifluoroprop-1-en-1yl)-2,2-dimethylcyclopropane carboxylate (m.p. 75°-76° C.).

N.m.r. (CDCl$_3$): 1.10 (t,6H); 1.30 (s,6H); 1.90-2.27 (m,2H); 2.60 (q,4H); 3.80 (m,2H); 5.28 (m,2H); 6.96 (d,1H) ppm.

Infra red (liquid parafin): 3070, 1730, 1650, 1490, 1270, 1200, 1140, 1050, 960, 870 cm$^{-1}$.

(vi) 4-ethylthiomethyl-2,3,5,6-tetrafluorobenzyl (±)-cis-3-(Z-2-chloro-3,3,3,-trifluoroprop-1-en-1yl)-2,2-dimethylcyclopropane carboxylate.

N.m.r. (CDCl$_3$): 1.18-1.46 (m,9H); 1.88-2.36 (m,2H); 2.58 (q,2H); 3.82 (s,2H); 5.22 (s,2H); 6.95 (d,1H) ppm.

Infra red (liquid film): 3080, 1735, 1655, 1490, 1135 cm$^{-1}$.

EXAMPLE 19 The procedure of Example 17 was also used to prepare the following products from ester (±)-cis-3-(Z-2-chloro-3,3,3-trifluoroprop-len-1yl)-2,2-dimethylcyclopropane carboxyclic acid or (±)-cis or (±)-trans-3-(2,3,3,3-tetrafluoroprop-lan-1-yl)-2,2-dimethylcyclopropane carboxylic acid and the appropriate benzyl alcohol. The n.m.r. and infra-red spectra of the products were consistent with the designated structures corresponding to the following:

(i) 4-dimethylaminomethyl-2,3,5,6-tetrafluorobenzyl (±)-cis-3-(Z-2-chloro-3,3,3-trifluoroprop-1-en-1-yl)-2,2-dimethylcyclopropane carboxylate.

(ii) 4-ethanesulphonylmethyl-2,3,5,6-tetrafluorobenzyl (±)-cis-3-(Z-2-chloro-3,3,3-trifluoroprop-1-en-1-yl)-2,2-dimethylcyclopropane carboxylate.
(iii) 4-methylaminomethyl-2,3,5,6-tetrafluorobenzyl (±)-cis-3-(Z-2-chloro-3,3,3-trifluoroprop-1-en-1-yl)-2,2-dimethylcyclopropane carboxylate.
(iv) 4-ethylaminomethyl-2,3,5,6-tetrafluorobenzyl (±)-cis-(Z-2-chloro-3,3,3-trifluoroprop-1-en-1-yl)-2,2dimethylcyclopropane carboxylate.
(v) 4-methylthiomethyl-2,3,5,6-tetrafluorobenzyl (±)-cis-(Z-2-chloro-3,3,3-trifluoroprop-1-en-1-yl)-2,2dimethylcyclopropane carboxylate.
(vi) 4-methanesulphinylmethyl-2,3,5,6-tetrafluorobenzyl (±)-cis-3-(Z-2-chloro-3,3,3-trifluoroprop-1-en-1-yl)-2,2-dimethylcyclopropane carboxylate.
(vii) 4-methoxymethyl-2,3,5,6-tetrafluorobenzyl (±)-cis-3-(Z-2,3,3,3-tetrafluoroprop-1-en-1-yl)-2,2dimethylcyclopropane carboxylate.
(viii) 4-methoxymethyl-2,3,5,6-tetrafluorobenzyl (±)-trans-3-(Z-2,3,3,3-tetrafluoroprop-1-en-1-yl)-2,2dimethylcyclopropane carboxylate (contaminated with ca. 10% of the cis isomer).

I claim:

1. The (+)-cis isomer of a compound of the formula

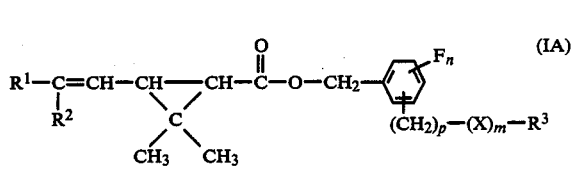

wherein $R^1$ is halomethyl, $R^2$ is halo, n is 4, p and m are both zero, $R^3$ is lower alkyl.

2. A compound according to claim 1 wherein $R^1$ is trifluoromethyl, $R^2$ is chloro.

3. A single isomer according to claim 2 wherein $R^3$ is methyl.

4. An insecticidal composition comprising an insecticidally effective amount of a compound according to claim 1 in association with an agriculturally acceptable diluent or carrier material.

5. A composition according to claim 5 in the form of granules of inert carried coated or impregnated with a compound according to claim 1.

6. A method of combating insect pests at a locus in which an insecticidally effective amount of a composition according to claim 4 is applied to the locus.

7. A method of combating soil dwelling insect pests in which an insecticidally effective amount of a composition according to claim 5 is applied to the soil.

8. The method of claim 7 in which the pests are rootworms of the genus Diabrotica.

* * * * *